(12) United States Patent
Kumasaka et al.

(10) Patent No.: US 6,875,202 B2
(45) Date of Patent: Apr. 5, 2005

(54) ELASTICALLY STRETCHABLE DISPOSABLE PANTS

(75) Inventors: Yoshinori Kumasaka, Kagawa-ken (JP); Hiroki Yamamoto, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 51 days.

(21) Appl. No.: 09/976,312

(22) Filed: Oct. 11, 2001

(65) Prior Publication Data

US 2002/0045874 A1 Apr. 18, 2002

(30) Foreign Application Priority Data

Oct. 13, 2000 (JP) ........................................ 2000-314187

(51) Int. Cl.⁷ ................................................. A61F 13/15
(52) U.S. Cl. ............................. 604/385.22; 604/385.24
(58) Field of Search ............ 604/385.22, 305.24–385.3, 604/379, 380

(56) References Cited

U.S. PATENT DOCUMENTS

| | | |
|---|---|---|
| 4,450,026 A | 5/1984 | Pieniak et al. |
| 4,486,192 A | 12/1984 | Sigl |
| 4,488,923 A | 12/1984 | Pieniak |
| 4,507,163 A | 3/1985 | Menard |
| 4,936,840 A * | 6/1990 | Proxmire ............... 604/385.22 |
| 4,940,464 A * | 7/1990 | Van Gompel et al. ...... 604/396 |
| 5,591,155 A * | 1/1997 | Nishikawa et al. ......... 604/393 |

FOREIGN PATENT DOCUMENTS

| | | |
|---|---|---|
| EP | 0 323 634 | 7/1989 |
| EP | 0 650 714 A1 | 5/1995 |
| JP | 7-155344 | 6/1995 |

* cited by examiner

Primary Examiner—Larry I. Schwartz
Assistant Examiner—C. Lynne Anderson
(74) Attorney, Agent, or Firm—Butzel Long

(57) ABSTRACT

Elastically stretchable disposable pants that include first and second lateral waist regions, which are formed in at least a front waist region with substantially inelastic guide zones arranged intermittently in the longitudinal direction. The pants thus constructed can be smoothly pulled up to a desired level at which the pants are properly worn.

13 Claims, 7 Drawing Sheets

ELASTICALLY STRETCHABLE DISPOSABLE PANTS

BACKGROUND OF THE INVENTION

This invention relates to elastically stretchable disposable pants such as a diaper, incontinent pants or the like.

Japanese Patent Application Publication No. 1995-155344A describes disposable pants comprising an elastically stretchable pants' basic structure and a pad member having a liquid-pervious topsheet, a liquid-impervious backsheet and a liquid-absorbent core disposed between the two sheets wherein the pad member is attached to the inner surface of the pants' basic structure. The pants' basic structure comprises a laminated composite sheet of elastically stretchable fibrous nonwoven fabric and elastically stretchable plastic film and has an omnidirectional stretchability. The pants' basic structure is composed of a front waist region, a rear waist region opposed to the front waist region, and first and second lateral waist regions extending between the front and rear waist regions in a waist-surrounding direction, respectively. Transversely opposite side edge portions of the pants' basic structure corresponding to those of the first and second lateral waist regions are bonded together so as to define a waist-opening and a pair of leg-openings.

The Publication describes a manner in which the pants are worn by a wearer him- or herself as follows: The wearer inserts his or her legs into the leg-openings of the pants' basic structure and then pulls up the pants around his or her waist with the first and second lateral waist regions of the pants' basic structure grasped by fingers. However, here is a problem due to the omnidirectional stretchability of the pants' basic structure such that a friction generated between the pants and the wearer's skin as the pants' basic structure is pulled up causes the first and second lateral waist regions of the pants' basic structure to be more stretched upward than the front and rear waist regions. Consequently, the front and rear waist regions may often remain below the first and second lateral waist regions being pulled up. In other words, it may be often necessary for the wearer to pull up the front and rear waist regions after the first and second lateral waist regions have been pulled up. Thus such pants of prior art takes much time to wear them.

SUMMARY OF THE INVENTION

It is an object of this invention to provide elastically stretchable disposable pants made of elastically stretchable sheet members designed so that the pants can be smoothly pulled up to a desired level at which the pants are properly worn.

According to this invention, there is provided elastically stretchable disposable pants having a longitudinal axis comprising: being made of elastically stretchable sheet members; a front waist region; a rear waist region opposed to the front waist region; a waist-opening and a pair of leg-openings defined by the front and rear waist regions jointed at side edge portions thereof to each other.

According to this invention each of substantially inelastic guide zones are provided between the longitudinal axis and each of the side edges of the front and rear waist regions, extending longitudinal of the pants between vicinity of a peripheral edge portion of the waist-opening and vicinity of each of the leg-openings.

According to one embodiment of this invention, the sheet members comprise layers of elastically stretchable fibrous nonwoven fabric and the nonwoven fabric is molten and solidified so that the guide zones have substantially no elastic stretchability.

According to another embodiment of this invention, the sheet members comprise layers of elastically stretchable fibrous nonwoven fabric and inelastic strips of sheet are bonded to the guide zones with the nonwoven fabric being not stretched so that the guide zones have substantially no elastic stretchability.

According to still another embodiment of this invention, a pad member comprising a liquid-pervious topsheet, a liquid-impervious backsheet and a liquid-absorbent core disposed between the top- and backsheets is attached to the inner surface of the pants and extend from the front waist to the rear waist region.

According to further another embodiment of this invention, the pants comprise a liquid-pervious topsheet, a liquid-impervious backsheet and a liquid-absorbent core disposed between the top- and backsheets and extending from the front waist region to the rear waist region and wherein at least the backsheet of the top- and backsheets is formed with the sheet members.

DETAILED DESCRIPTION OF THE PREFERRED EMBODIMENTS

Details of an elastically stretchable disposable pants will be more fully understood from the description given hereunder with reference to the accompanying drawings.

Figure 1:
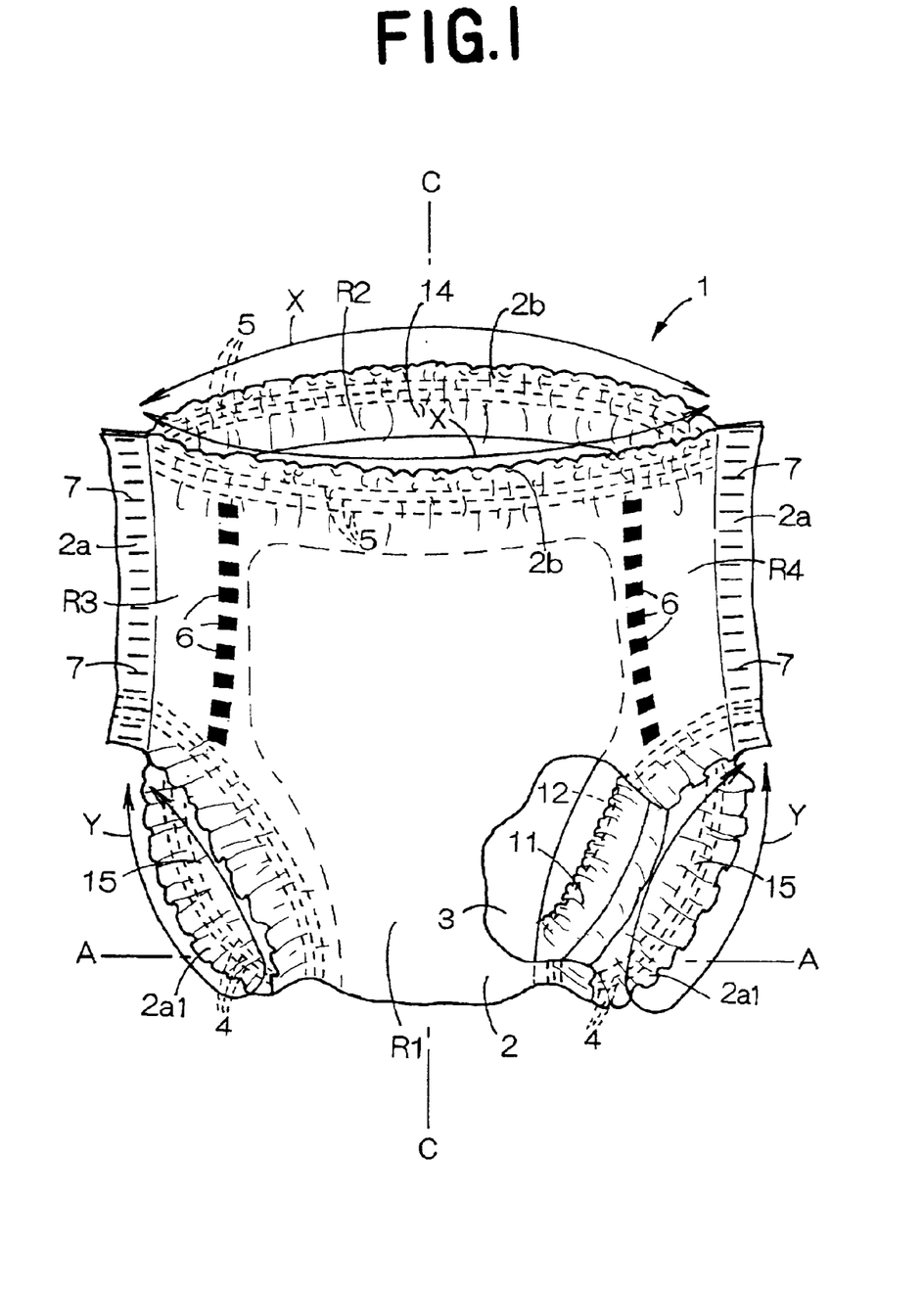
FIG. 1 is a perspective view showing one embodiment of the disposable pants according to this invention as partially broken away.
Figure 2:
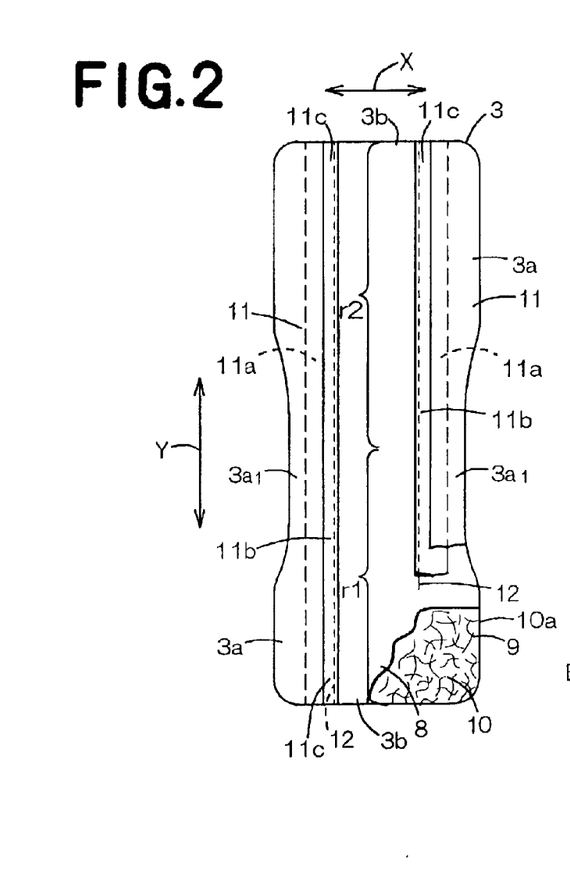
FIG. 2 is a plan view showing the pants with a basic structure thereof and a pad member separated from each other.

FIG. 1 is a perspective view showing one embodiment of disposable pants according to this invention as partially broken away and FIG. 2 is a plan view showing the pants 1 with the pants' basic structure 2 and the pad member 3 separated from each other by disconnecting lateral waist regions R3, R4 of the pants basic structure 2 from the pad member 3. The pant's basic structure 2 and the pad member 3 are formed symmetrically with respect to a longitudinal axis C. Referring to FIG. 1, a waist-surrounding direction is indicated by an arrow X and a leg-surrounding direction is indicated by an arrow Y. Referring to FIG. 2, a transverse direction is indicated by an arrow X and a longitudinal direction is indicated by an arrow Y. The expression used herein "inner surfaces" of the pants' basic structure 2 as well as of the top- and backsheets 8, 9 should be understood to be the surfaces facing the core 10 and the expression used herein "outer surfaces" thereof should be understood to be the surfaces thereof not facing the core 10. The pants 1 comprise the pants' basic structure 2 and the pad member 3 attached to the inner surface of the pants' basic structure 2.

The pants' basic structure 2 is formed with two layers of elastically stretchable hydrophobic fibrous nonwoven fabric having surfaces thereof facing each other intermittently bonded together. Alternatively, the pants' basic structure 2 may be formed with a composite sheet consisting of elastically stretchable hydrophobic fibrous nonwoven fabric and elastically stretchable plastic film laminated with the nonwoven fabric.

The pants' basic structure 2 has a front waist region R1, a rear waist region R2 opposed to the front waist region R1 and first and second lateral waist regions R3, R4 extending in a waist surrounding direction between the front and rear waist regions R1, R2, respectively. The pants' basic structure 2 define a waist-opening 14 and a pair of leg-openings 15.

As seen in FIG. 2, the pants' basic structure 2 has transversely opposite side edge portions 2a extending in the longitudinal direction and longitudinally opposite end portions 2b extending in parallel to each other in the transverse direction. Longitudinally middle sections $2a_1$ of the respective side edge portions 2a curve inward in the transverse direction of the pants' basic structure 2 so as to describe circular arcs. The pants' basic structure 2 is elastically stretchable not only in its longitudinal direction but also in its transverse direction.

The longitudinally middle sections $2a_1$ of the respective side edge portions 2a are provided with elastic members 4 bonded under tension thereto to be associated with the respective leg-openings. Each of the elastic members 4 comprises a plurality of elastic elements being elastically stretchable in the longitudinal direction. The longitudinally opposite end portions 2b are provided with elastic members 5 bonded under tension thereto to be associated with the waist-opening. Each of the elastic members 5 comprises a plurality of elastic elements being elastically stretchable in the transverse direction. Both the elastic members 4 associated with the leg-openings and the elastic members 5 associated with the waist-opening are disposed between the layers of nonwoven fabric forming the pants' basic structure and bonded to these layers of nonwoven fabric.

The first and second lateral waist regions R3, R4 in the pants 1 of this invention are, more specifically to define, the regions extending between the transversely opposite side edge portions 2a of the pants' basic structure 2 and transversely opposite side edge portions 3a of the pad member 3 which will be described more in details, respectively.

In the pants' basic structure 2, its transversely opposite side edge portions 2a except the longitudinally middle sections $2a_1$ thereof are put flat and bonded together in a plurality of bonding zones 7 intermittently arranged in the longitudinal direction so as to shape the pants' basic structure 2 into the pants.

In the pants' basic structure 2, the longitudinally middle sections $2a_1$ of the respective side edge portions 2a define the peripheral edge portions $2a_1$ of the respective leg-openings 15 and the longitudinally opposite end portions 2b of the pants' basic structure 2 define the peripheral edge portion 2b of the waist-opening 14, as will be apparent from FIG. 1. The elastic members 4 associated with the respective leg-openings 15 extend along the peripheral edge portions $2a_1$, respectively, in the leg-surrounding direction. The elastic members 5 associated with the waist-opening 14 extends along the peripheral edge portion 2b in the waist-surrounding direction.

The first and second lateral waist regions R3, R4 are formed at locations put aside to the front waist region R1 with a plurality of substantially inelastic guide zones 6. More specifically, these guide zones 6 are intermittently arranged in the longitudinal direction between the vicinity of the peripheral edge portion 2b of the waist-opening 14 and the vicinity of the peripheral edge portions $2a_1$ of the leg-openings 15. In these guide zones 6, the nonwoven fabric has been molten and thereafter solidified, so the nonwoven fabric in the zones has substantially no elastic stretchability. In these guide zones 6, the nonwoven fabric is no more fibrous and presents a film-like state. In an alternative arrangement, these guide zones 6 may be partially placed upon the side edge portions 3b of the pad member 3.

The pad member 3 comprises a liquid-pervious topsheet 8 made of a hydrophilic fibrous nonwoven fabric or a porous plastic film, a liquid-impervious backsheet 9 made of a hydrophobic fibrous nonwoven fabric, a liquid-impervious plastic film or a laminated composite sheet consisting of the hydrophobic fibrous nonwoven fabric and the plastic film laminated, a liquid-absorbent core 10 disposed between the top- and backsheets 8, 9, and a pair of substantially liquid-impervious leakage-barrier cuffs 11 made of a hydrophobic fibrous nonwoven fabric. The core 10 is entirely covered with and bonded to tissue paper (not shown) and bonded to the inner surfaces of the top- and backsheets 8, 9 with the tissue paper therebetween.

As seen in FIG. 2, the pad member 3 is contoured by transversely opposite side edge portions 3a extending in the longitudinal direction and longitudinally opposite end portions 3b extending in the transverse direction and generally comprises a front region r1 and a rear region r2. Longitudinally middle sections $3a_1$ of the respective side edge portions 3a curve inward in the transverse direction of the pad member 3 so as to describe circular arcs. As indicated by chain lines in FIG. 2, the front region r1 lies in the front waist region R1 of the pants' basic structure 2 and the rear region r2 lies in the rear waist region R2 of the pants' basic structure 2. The outer surface of the backsheet 9 constituting the pad member 3 is bonded to the pants' basic structure 2 in a bonding zone 13 extending on the inner surface of the pants' basic structure 2 as indicated by an chain line.

Each of the cuffs 11 has a fixed side edge portion 11a extending in the longitudinal direction along the associated side edge portion 10a of the core 10, a free side edge portion 11*b* being contiguous to the fixed side edge portion 11*a* and normally biased to rise on the topsheet 8 and longitudinally opposite fixed end portions 11*c* collapsed inward in the transverse direction of the pad member 3 onto the topsheet 8. The free side edge portion 11*b* is provided with an elastic member 12 being stretchable in the longitudinal direction and bonded under tension to the free side edge portion 11*b*. The elastic member 12 is covered with a part of the free side edge portion 11*b*.

To wear the pants 1, the wearer may insert his or her legs into the respective leg-openings 15 of the pants' basic structure 2 and pull the pants 1 up to his or her waist by grasping the first and second lateral waist regions R3, R4 with his or her fingers. In the pants' basic structure 2, movement of the guide zones 6 in the longitudinal direction causes the region extending in the vicinity of these guide zones 6 to move in the longitudinal direction. When this pants 1 is worn, the front waist region R1 also is pulled up following the movement of the guide zones 6 as the first and second lateral waist regions R3, R4 are pulled up, so it is not apprehended that the front waist region R1 might remain below the first and second lateral waist regions R3, R4 as the first and second lateral waist regions R3, R4 are pulled up to wear the pants 1. In other words, the front waist region R1 can be pulled together with the first and second lateral waist regions R3, R4 up to the desired level.

Figure 3:
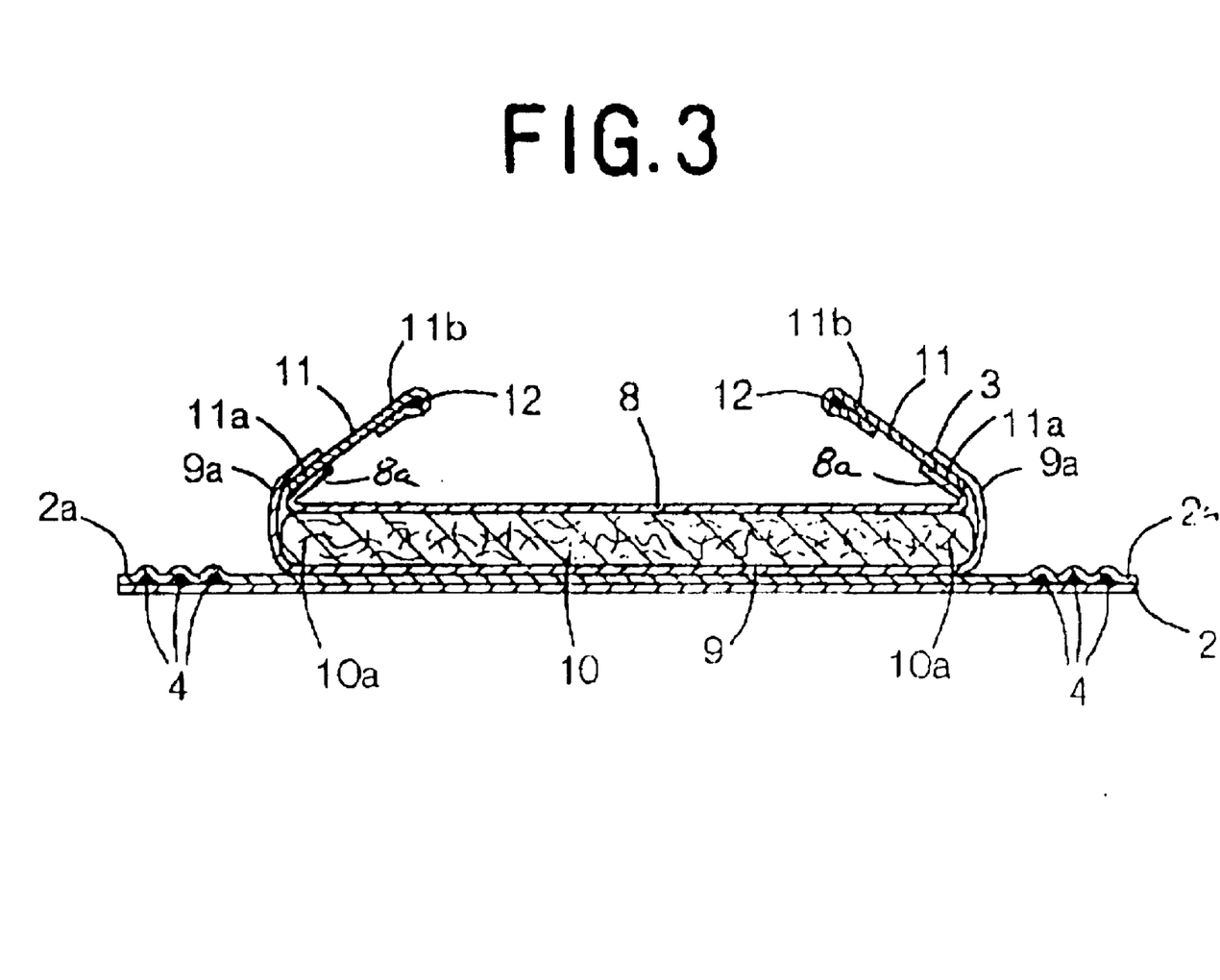
FIG. 3 is a sectional view taken along a line A—A in FIG. 1.
Figure 4:
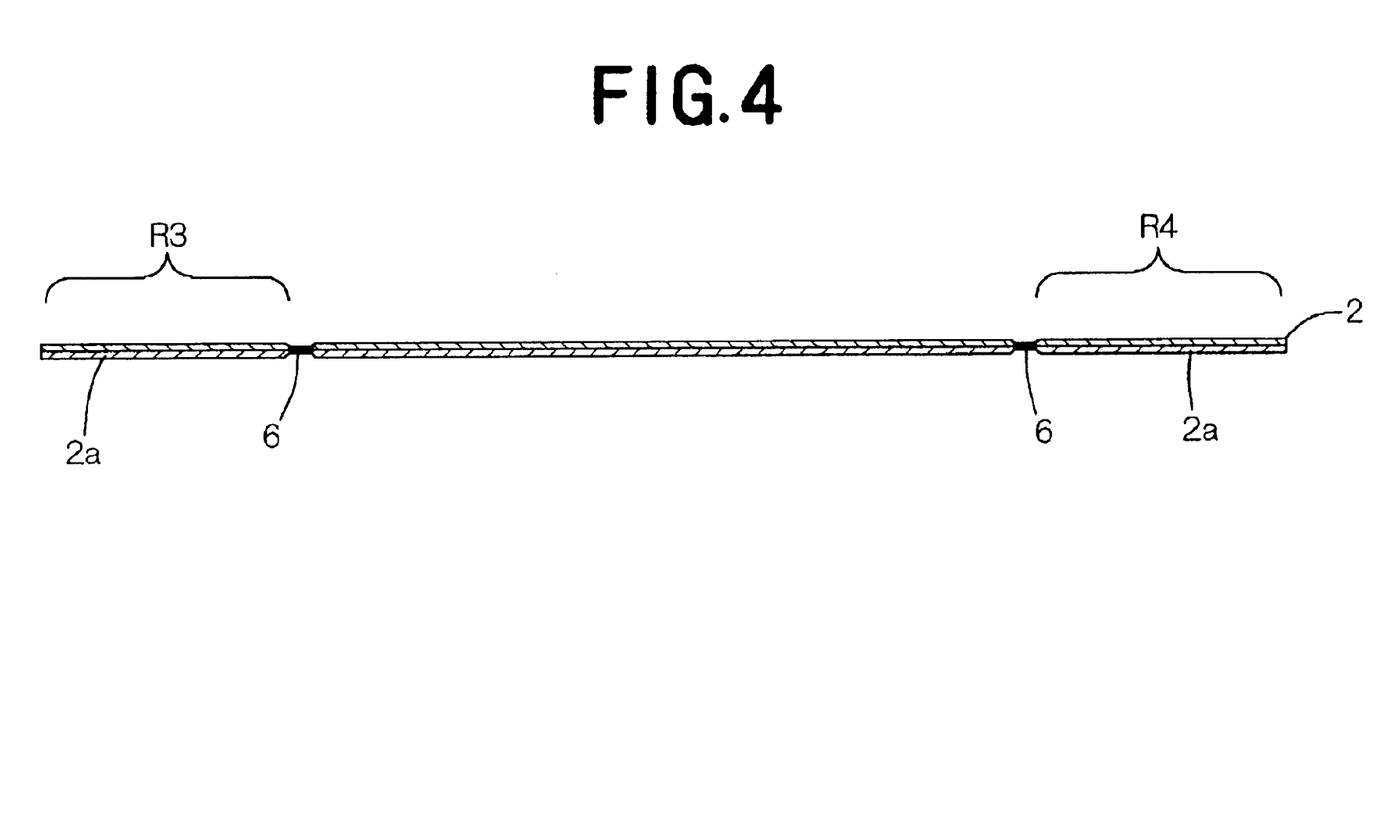
FIG. 4 is a sectional view taken along a line B—B in FIG. 2.

FIG. 3 is a sectional view taken along a line A—A in FIG. 1 and FIG. 4 is a sectional view taken along a line B—B in FIG. 2. Of the pad member 3, transversely opposite side edge portions 8*a* of the topsheet 8 and transversely opposite side edge portions 9*a* extend outward beyond transversely opposite side edges 10*a* of the core 10. The side edge portions 9*a* are folded back along the side edges 10*a* of the core 10 toward the outer surface of the topsheet 8. The fixed side edge portions 11*a* of the respective cuffs 11 are disposed between the side edge portions 8*a* and side edge portions 9*a*, respectively, and bonded to the inner surfaces of these side edge portions 8*a*, 9*a*. The longitudinal opposite fixed end portions 11*c* of the respective cuffs 11 are bonded to the outer surface of the topsheet 8 (See FIG. 2).

The pad member 3 is curved, in the longitudinal direction, with the topsheet 8 inside and contraction of the elastic members 11 causes the respective free side edge portions 11*b* to rise on the topsheet 8. In the pad member 3, the free side edge portions 11*b* of the respective cuffs 11 define barriers functioning to prevent leakage of excretion from the side edge portions 3*a* of the pad member 3.

Figure 5:
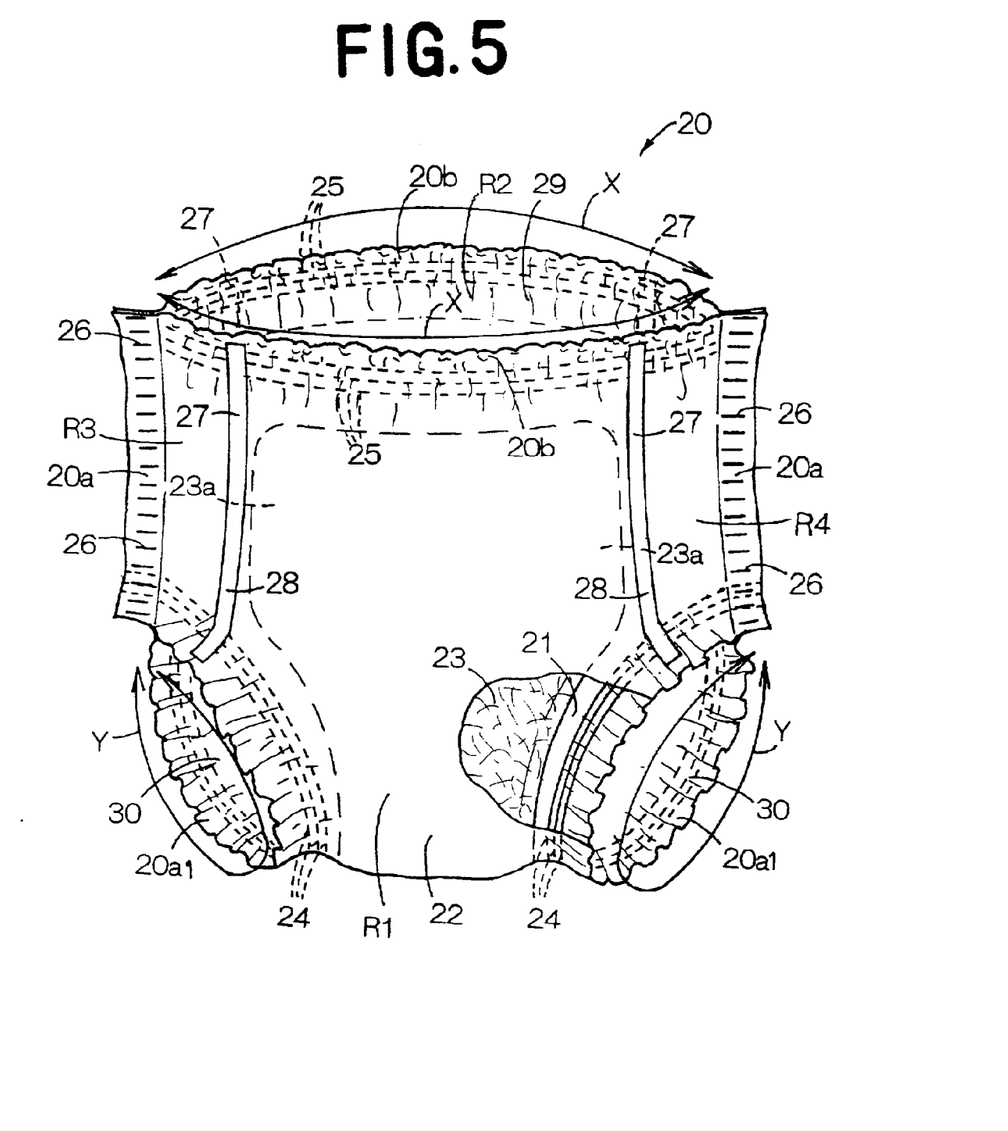
FIG. 5 is a perspective view showing another embodiment of the disposable pants according to this invention as partially broken away.
Figure 6:
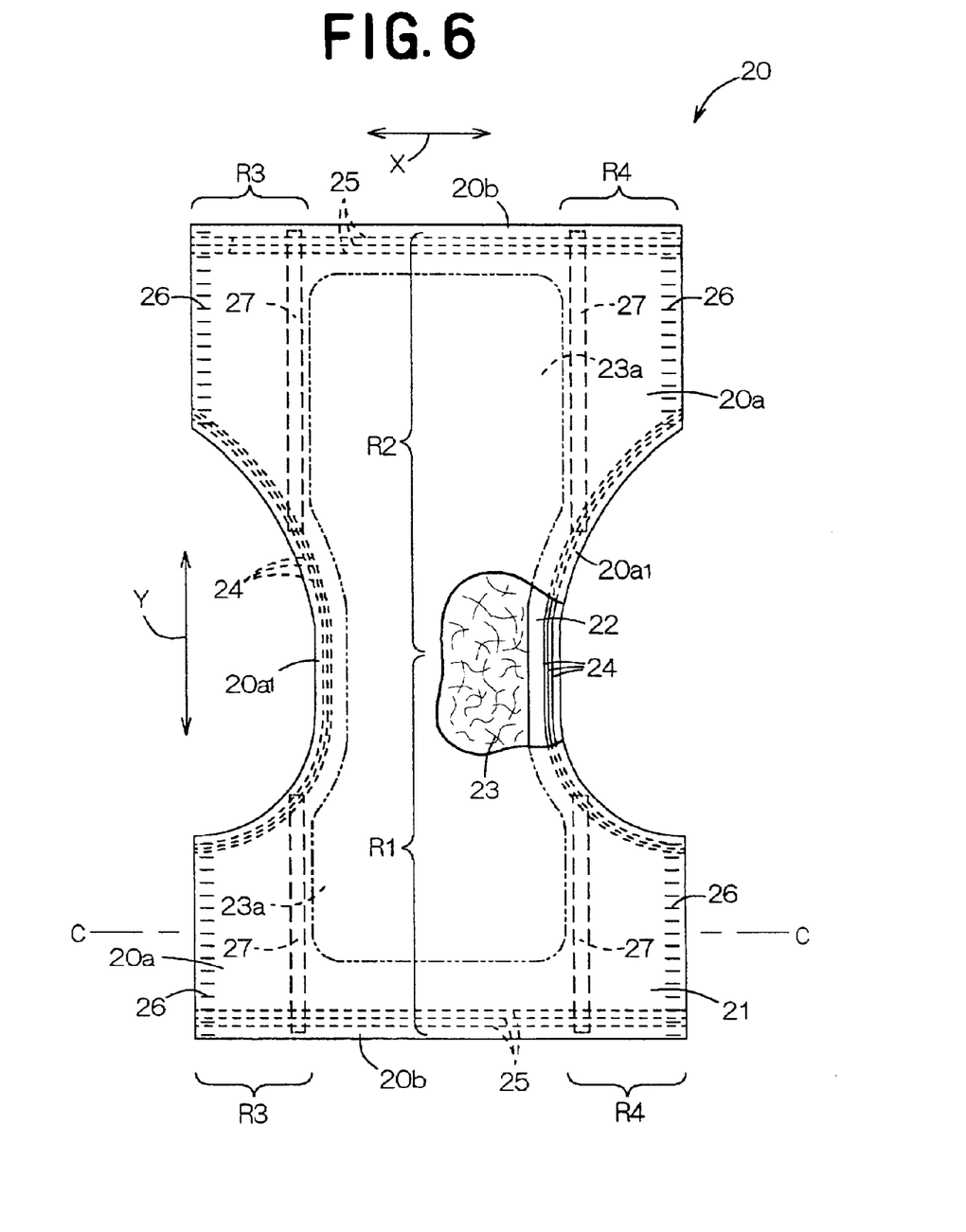
FIG. 6 is a plan view showing the pants as developed in the longitudinal direction as partially broken away.
Figure 7:
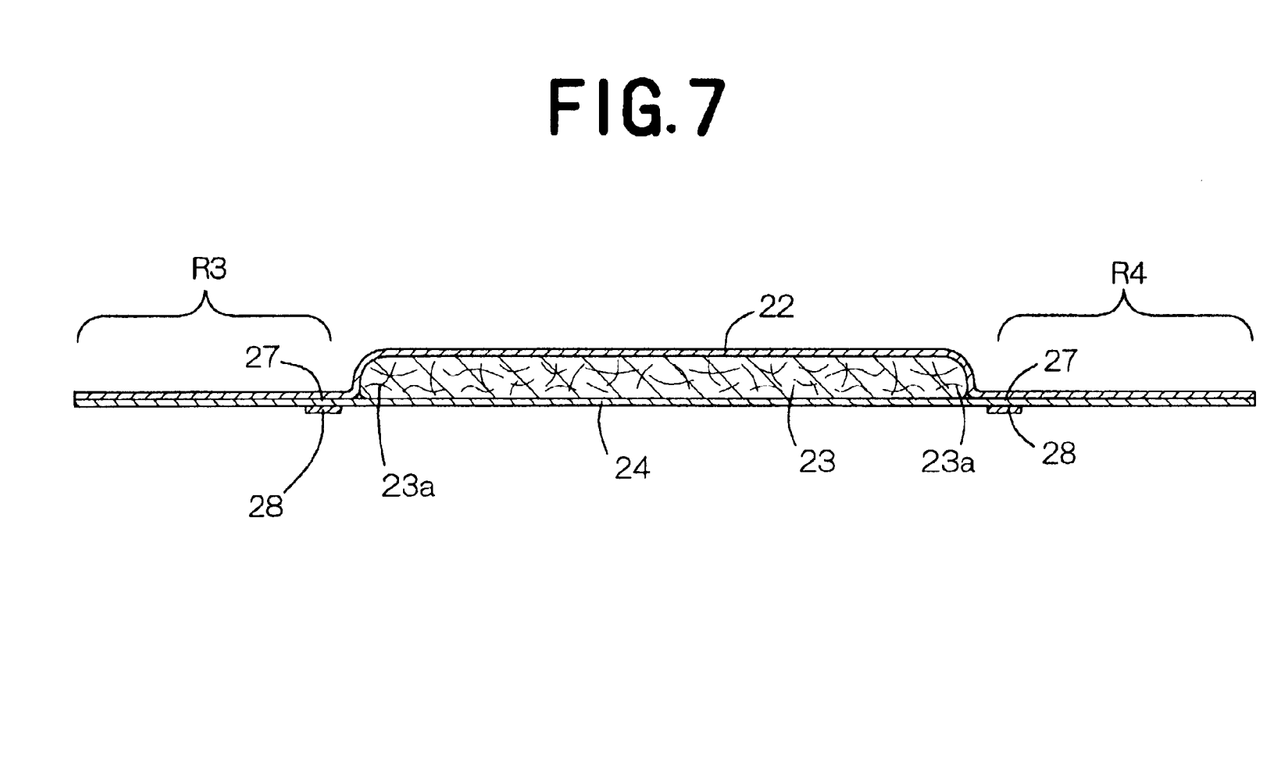
FIG. 7 is a sectional view taken along a line C—C in FIG. 6.

FIG. 5 is a perspective view showing another embodiment of the disposable pants 20 according to this invention as partially broken away, FIG. 6 is a plan view showing the pants 20 as developed in the longitudinal direction with the lateral waist regions R3, R4 having been disconnected from each other as partially broken away and FIG. 7 is a sectional view taken along a line C—C in FIG. 6.

The pants 20 comprise a liquid-previous topsheet 21 made of an elastically stretchable hydrophilic fibrous nonwoven fabric, a liquid-impervious backsheet 22 made of an elastically stretchable hydrophobic fibrous nonwoven fabric and a liquid-absorbent core 23 disposed between the top- and backsheets 21, 22 and entirely covered with and bonded to tissue paper (not shown). Alternatively, it is possible to use a laminated composite sheet consisting of elastically stretchable hydrophobic fibrous nonwoven fabric and elastically stretchable plastic film as stock material for the backsheet 22.

The topsheet 21 and the backsheet 22 have surfaces thereof placed upon and intermittently bonded to each other. The core 23 is intermittently bonded to the inner surfaces of the top- and backsheets 21, 22 with the tissue paper therebetween.

The pants 20 has a front waist region R1, a rear waist region R2 opposed to waist front waist region R1 and first and second lateral waist regions R3, R4 extending in a waist surrounding direction between the front and rear waist regions R1, R2, respectively. The pants 20 define a waist-opening 29 and a pair of leg-openings 30.

As seen in FIG. 6, the pants 20 has transversely opposite side edge portions 20*a* extending in the longitudinal direction and longitudinally opposite end portions 20*b* extending in parallel to each other in the transverse direction. Longitudinally middle sections $20a_1$ of the respective side edge portions 20*a* curve inward in the transverse direction of the pants 20 so as to describe circular arcs. The pants 20 is elastically stretchable not only in its longitudinal direction but also in its transverse direction.

The longitudinally middle sections $20a_1$ of the respective side edge portions 20*a* are provided with elastic members 24 bonded under tension thereto to be associated with the respective leg-openings. Each of the elastic members 24 comprises a plurality of elastic elements being elastically stretchable in the longitudinal direction. The longitudinally opposite end portions 20*b* are provided with elastic members 25 bonded under tension thereto to be associated with the waist-opening. Each of the elastic members 25 comprises a plurality of elastic elements being elastically stretchable in the transverse direction. Both the elastic members 24 associated with the leg-openings and the elastic members 25 associated with the waist-opening are disposed between the top- and backsheets 21, 22 and bonded to these sheets 21, 22.

The first and second lateral waist regions R3, R4 in the pants 20 are, more specifically to define, the regions extending between the transversely opposite side edge portions 20*a* of the pants 20 and transversely opposite side edge portions 23*a* of the core 23, respectively.

In the pants 20, its transversely opposite side edge portions 20*a* except the longitudinally middle sections $20a_1$ thereof are put flat and bonded together in a plurality of bonding zones 26 intermittently arranged in the longitudinal direction so as to obtain the desired pants-type.

The first and second lateral waist regions R3, R4 are formed at locations put aside to the and rear waist regions R1, R2 with a plurality of substantially inelastic guide zones 27, respectively. In these guide zones 27, inelastic strips of sheet 28 are bonded to the outer surface of the backsheet 22. These strips of sheet 28 are bonded to the backsheet 22 with both the topsheet 21 and the backsheet 22 being not stretched. These strips of sheet 28 vertically extend between the peripheral edge 20*b* of the waist-opening 29 and the peripheral edges $20a_1$ of the respective leg-openings 30. Alternatively, it is possible to bond the respective strips of sheet 28 to the outer surface of the topsheet 21 or to dispose these strips of sheet 28 between the top- and backsheets 21, 22 and to bond them to the inner surfaces of these top- and backsheets 21, 22.

Inelastic fibrous nonwoven fabric or a flexible and inelastic plastic sheet may be used as stock material for the strips of sheet 28. The guide zones 27 may be formed by coating the inner surfaces of the top- and backsheets 21, 22 with inelastic adhesive and bonding these top- and backsheets 21, 22 to each other.

To wear the pants 20, the wearer pulls the first and second lateral waist regions R3, R4 so that movement of the guide zones 27 in the longitudinal direction causes the front and rear waist regions R1, R2. In this way, the front and rear waist regions R1, R2 also are pulled up following the movement of the guide zones 27 as the first and second lateral waist regions R3, R4 are pulled up, so the front and rear waist regions R1, R2 can be pulled up together with the lateral waist regions R3, R4 to the desired level without any anxiety that the front and rear waist regions R1, R2 might remain below the first and second lateral waist regions R3, R4.

The elastic stretchable nonwoven fabric may be selected from a group including those obtained by melt blown—or spun bond process. Component fiber of such nonwoven fabric may be stretchable fiber obtained by melt spinning thermoplastic elastomer resin. It is also possible to use, for this purpose, composite nonwoven fabric consisting of the nonwoven fabric made of thermoplastic elastomer resin fiber and the nonwoven fabric made of crimped fiber obtained by melt spinning thermoplastic synthetic resin such as polypropylene, polyethylene or polyester laminated on at least one surface of the first-mentioned nonwoven fabric.

The nonwoven fabric used as stock material for the top- and backsheets 8, 9 as well as the cuffs 11 of the pad member 3 may be selected from those obtained by spun lace-, needle punch-, melt blown-, thermal bond-, spun bond-, chemical bond- and air through-processes. Component fiber of the nonwoven fabric may be selected from a group including polyolefine-, polyester- and polyamide-based fibers and polyethylene/polypropylene or polyethylene/polyester core-sheath type conjugated fiber and side-by-side-type conjugated fiber.

The cores 10, 23 are a mixture of fluff pulp, high absorption polymer particles and thermoplastic synthetic resin fiber compressed to a desired thickness. The polymer particles may be selected from a group including starch-, cellulose-based polymer and synthetic polymer.

To bond the pants' basic structure 2 of the pants to the pad member 3, the top- and backsheets 8, 9, 21, 22 one to another, the leakage-barrier cuffs 11 as well as the core 10 to the top- and backsheets 8, 9, the core 23 to the top- and backsheets 21, 22 and to attach the elastic members 4, 5, 12, 24, 25 to the pants, suitable adhesive such as hot melt adhesive or welding means such as heat-sealing or ultrasonic sealing may be used.

The disposable pants according to this invention includes first and second lateral waist regions that are formed at locations put aside toward at least one of the front and rear waist regions with the substantially inelastic guide zones arranged in the longitudinal direction. Movement of the guide zones in the longitudinal direction causes the region extending in the vicinity of these guide zones to move in the longitudinal direction. The front and rear waist regions also are pulled up following the movement of the guide zones as the first and second lateral waist regions are pulled up to wear the pants, so the front and rear waist regions can be pulled up together with the lateral waist regions to the desired level without any anxiety that the front and rear waist regions might remain below the first and second lateral waist regions. In this way, the pants can be more smoothly pulled up to the desired level around the wearer's waist.

What is claimed is:

1. Elastically stretchable disposable pants having a ventral longitudinal axis and comprising:
    a pair of elastically stretchable sheet members;
    a front waist region having side edges;
    a rear waist region opposed to said front waist region;
    a waist-opening and a pair of leg-openings defined by bonding said front and rear waist regions at edge portions thereof to each other; and
    a pair of spaced apart substantially inelastic guide zones provided between said central longitudinal axis and each of said side edges of said front and rear waist regions, and extending longitudinally of said pants between said waist-opening and each of each of said leg-openings, each of said substantially inelastic guide zones of said pair of substantially inelastic guide zones comprising a discrete array of discrete inelastic portions of the elastically stretchable sheet members, said discrete arrays having upper terminal ends which terminate near the waist-opening and lower terminal ends that are spaced apart from the leg-openings, said substantially inelastic guide zones being configured to prevent portions of the disposable diaper in a vicinity of the substantially inelastic guide zones from stretching along a direction parallel to the central longitudinal axis.

2. The pants according to claim 1, wherein said pair of elastically stretchable sheet members comprise layers of elastically stretchable fibrous nonwoven fabric and said substantially inelastic guide zones comprise portions of said nonwoven fabric which are molten and solidified so as to have substantially no elastic stretchability.

3. Elastically stretchable disposable pants comprising:
    a pair of elastically stretchable sheet members comprising layers of elastically stretchable fibrous nonwoven fabric;
    a front waist region having side edges;
    a rear waist region opposed to said front waist region;
    a waist-opening and a pair of leg-openings defined by bonding said front and rear waist regions at edge portions thereof to each other; and
substantially inelastic guide zones provided between said central longitudinal axis and each of said side edges of said front and rear waist regions, and extending longitudinally of said pants between said waist-opening and each of each of said leg-openings, said substantially inelastic guide zones comprising inelastic strips of sheet material that have surface areas and are superimposed over continuous surface areas of one of said non-woven fabrics which superimposed continuous surface areas are coextensive with the surface area of said substantially inelastic strips, said inelastic strips being bonded to said one of said nonwoven fabrics so as to be exposed on an outer surface of said pants and so that said substantially inelastic guide zones have substantially no elastic stretchability, said substantially inelastic guide zones being configured to prevent portions of the disposable diaper in a vicinity of the substantially inelastic guide zones from stretching along a direction parallel to the central longitudinal axis.

4. The pants according to claim 1, wherein a pad member comprising a liquid-pervious topsheet, a liquid-impervious backsheet and a liquid-absorbent core disposed between said liquid-pervious topsheet and said liquid-impervious backsheet is attached to an inner surface of said pants and extends from said front waist region to said rear waist region.

5. The pants according to claim 1, wherein said pants comprise a liquid-pervious topsheet, a liquid-impervious backsheet and a liquid-absorbent core disposed between said liquid-pervious topsheet and said liquid-impervious backsheet and extending from said front waist region to said rear waist region, and of said liquid-imperious backsheet and said liquid-pervious topsheet at least said liquid-impervious backsheet is formed from said pair of elastically stretchable sheet members.

6. The pants according to claim 1, wherein each of said substantially inelastic guide zones is located aside toward said side edges of said front and rear waist regions.

7. The pants according to claim 4, wherein each of said substantially inelastic guide zones is located in a vicinity of said pad member.

8. The pants according to claim 1, wherein the upper terminal ends of the inelastic zones are spaced apart from the waist-opening.

9. The pants according to claim 1, wherein the array of discrete inelastic portions of the elastically stretchable sheet members comprises a linear array.

10. The pants according to claim 2, wherein a pad member comprising a liquid-pervious topsheet, a liquid-impervious backsheet and a liquid-absorbent core disposed between said liquid-pervious topsheet and said liquid-impervious backsheet is attached to an inner surface of said pants and extends from said front waist region to said rear waist region.

11. The pants according to claim 2, wherein said pants comprise a liquid-pervious topsheet, a liquid-impervious backsheet and a liquid-absorbent core disposed between said liquid-pervious topsheet and said liquid-impervious backsheet and extending from said front waist region to said rear waist region, and of said liquid-imperious backsheet and said liquid-pervious topsheet at least said liquid-impervious backsheet is formed from said pair of elastically stretchable sheet members.

12. The pants according to claim 2, wherein each of said substantially inelastic guide zones is located aside toward said side edges of said front and rear waist regions.

13. The pants according to claim 10, wherein each of said substantially inelastic guide zones is located in a vicinity of said pad member.

* * * * *